United States Patent
Ganapati et al.

(10) Patent No.: US 10,937,179 B2
(45) Date of Patent: *Mar. 2, 2021

(54) SYSTEM AND METHOD FOR 3D SCENE RECONSTRUCTION WITH DUAL COMPLEMENTARY PATTERN ILLUMINATION

(71) Applicant: Verily Life Sciences LLC, Mountain View, CA (US)

(72) Inventors: Vidya Ganapati, San Jose, CA (US); Eden Rephaeli, Oakland, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/522,530

(22) Filed: Jul. 25, 2019

(65) Prior Publication Data
US 2019/0347814 A1 Nov. 14, 2019

Related U.S. Application Data

(63) Continuation of application No. 15/487,114, filed on Apr. 13, 2017, now Pat. No. 10,410,365.
(Continued)

(51) Int. Cl.
*H04N 7/18* (2006.01)
*G06T 7/521* (2017.01)
(Continued)

(52) U.S. Cl.
CPC ............ *G06T 7/521* (2017.01); *A61B 1/0002* (2013.01); *A61B 1/0005* (2013.01);
(Continued)

(58) Field of Classification Search
CPC .. A61K 9/5089; A61K 9/5026; A61K 9/5073; A61K 9/5115; A61K 9/5153
(Continued)

(56) References Cited

U.S. PATENT DOCUMENTS

| 4,648,717 A | 3/1987 | Ross et al. |
| 4,805,027 A | 2/1989 | Sluyter |

(Continued)

FOREIGN PATENT DOCUMENTS

| JP | 2004-294390 A | 10/2004 |
| JP | 2011-7576 A | 1/2011 |

(Continued)

OTHER PUBLICATIONS

Feng et al, Digital micromirror device camera used for high speed and high resolution imaging (Year: 2016).*
(Continued)

*Primary Examiner* — Shan E Elahi
(74) *Attorney, Agent, or Firm* — Christensen O'Connor Johnson Kindness PLLC

(57) ABSTRACT

An apparatus, system and process for utilizing dual complementary pattern illumination of a scene when performing depth reconstruction of the scene are described. The method may include projecting a first reference image and a complementary second reference image on a scene, and capturing first image data and second image data including the first reference image and the complementary second reference image on the scene. The method may also include identifying features of the first reference image from features of the complementary second reference image. Furthermore, the method may include performing three-dimensional (3D) scene reconstruction for image data captured by the imaging device based on the identified features in the first reference image.

22 Claims, 10 Drawing Sheets

Related U.S. Application Data

(60) Provisional application No. 62/344,789, filed on Jun. 2, 2016.

(51) Int. Cl.

| | | |
|---|---|---|
| *G06T 7/55* | (2017.01) | |
| *G01B 11/25* | (2006.01) | |
| *H04N 13/207* | (2018.01) | |
| *H04N 13/254* | (2018.01) | |
| *H04N 13/271* | (2018.01) | |
| *A61B 1/00* | (2006.01) | |
| *A61B 1/04* | (2006.01) | |
| *A61B 1/06* | (2006.01) | |
| *A61B 90/00* | (2016.01) | |

(52) U.S. Cl.
CPC ............ *A61B 1/00011* (2013.01); *A61B 1/04* (2013.01); *A61B 1/063* (2013.01); *G01B 11/2513* (2013.01); *G06T 7/55* (2017.01); *H04N 13/207* (2018.05); *H04N 13/254* (2018.05); *H04N 13/271* (2018.05); *A61B 2090/366* (2016.02); *G06T 2207/10068* (2013.01)

(58) Field of Classification Search
USPC ......................................................... 348/45
See application file for complete search history.

(56) References Cited

U.S. PATENT DOCUMENTS

| | | | | |
|---|---|---|---|---|
| 7,027,081 | B2* | 4/2006 | Kremen | H04N 19/00 348/51 |
| 8,013,904 | B2* | 9/2011 | Tan | H04N 9/3182 348/222.1 |
| 8,189,957 | B2* | 5/2012 | Tan | H04N 5/2628 348/51 |
| 8,218,003 | B2* | 7/2012 | Tan | G06T 3/00 348/135 |
| 8,411,932 | B2 | 4/2013 | Liu et al. | |
| 8,447,099 | B2 | 5/2013 | Wang et al. | |
| 9,753,542 | B2 | 9/2017 | Chizeck et al. | |
| 2002/0156349 | A1* | 10/2002 | Yamaki | A61B 1/0638 600/178 |
| 2003/0092470 | A1 | 5/2003 | Kurakane | |
| 2005/0083511 | A1 | 4/2005 | Markle | |
| 2005/0088435 | A1 | 4/2005 | Geng | |
| 2007/0065857 | A1* | 3/2007 | Glaser | G01N 21/314 435/6.11 |
| 2007/0165246 | A1 | 7/2007 | Kimmel | |
| 2010/0141780 | A1* | 6/2010 | Tan | H04N 9/3182 348/222.1 |
| 2010/0179420 | A1 | 7/2010 | Ernst | |
| 2010/0182311 | A1* | 7/2010 | Kim | H04N 13/254 345/419 |
| 2011/0050864 | A1 | 3/2011 | Bond | |
| 2011/0298960 | A1* | 12/2011 | Tan | H04N 9/3182 348/333.1 |
| 2012/0027290 | A1 | 2/2012 | Baheti et al. | |
| 2012/0176380 | A1 | 7/2012 | Wang et al. | |
| 2012/0176478 | A1 | 7/2012 | Wang et al. | |
| 2012/0177283 | A1 | 7/2012 | Wang et al. | |
| 2013/0127980 | A1* | 5/2013 | Haddick | G02B 27/0093 348/14.08 |
| 2013/0335535 | A1 | 12/2013 | Kane et al. | |
| 2014/0071131 | A1* | 3/2014 | Kitago | H04N 13/111 345/427 |
| 2014/0146131 | A1* | 5/2014 | Niemi | G03B 37/04 348/36 |
| 2014/0152769 | A1* | 6/2014 | Atwell | H04N 13/207 348/46 |
| 2014/0327885 | A1* | 11/2014 | Mansur | H04N 9/3126 353/31 |
| 2015/0003699 | A1* | 1/2015 | Davis | G16H 40/67 382/128 |
| 2015/0005640 | A1* | 1/2015 | Davis | G06T 5/40 600/476 |
| 2015/0005644 | A1* | 1/2015 | Rhoads | A61B 5/444 600/477 |
| 2015/0006186 | A1* | 1/2015 | Davis | A61B 5/6898 704/500 |
| 2015/0302594 | A1* | 10/2015 | Moore | G01B 11/25 348/47 |
| 2016/0015258 | A1 | 1/2016 | Levin et al. | |
| 2016/0295208 | A1* | 10/2016 | Beall | G06T 7/80 |
| 2016/0301922 | A1* | 10/2016 | Green | H04N 17/002 |
| 2019/0347814 | A1* | 11/2019 | Ganapati | A61B 1/00011 |

FOREIGN PATENT DOCUMENTS

| | | |
|---|---|---|
| JP | 2013-88260 A | 5/2013 |
| JP | 2013-534843 A | 9/2013 |
| JP | 2014-85257 A | 5/2014 |
| WO | 2016/071020 A1 | 5/2016 |

OTHER PUBLICATIONS

Chiranjan et al, Implementation of adaptive colded aperture imaging using a digital micro-mirror device for defocus deblurring (Year: 2016).*

Morita, H. et al., "Reconstruction of Surfaces of 3-D Objects by M-array Pattern Projection Method", Computer Vision, Second International Conference, IEEE, Dec. 5, 1988, pp. 468-473.

Morano, R.A. et al., "Short Papers Structured Light Using Pseudo-random Codes", IEEE Transactions on Pattern Analysis and Machine Intelligence, IEE Computer Society vol. 20, No. 1, Mar. 1, 1998, pp. 322-327.

PCT/US2017/031707, International Search Report and the Written Opinion of the International Searching Authority, dated Sep. 18, 2017, 21 pages.

Calagari et al., Data driven 2-D to 3-D video conversion for soccer (Year: 2018).

Hasegawa, Kazuhide et al., "Endoscope System for High Speed 3-D Measurement," The Transactions of the Institute of Electronics, Information and Communication Engineers, Japan, The Institute of Electronics, Information and Communication Engineers, Jan. 25, 2000, vol. J83-D-II, No. 1, pp. 271-279. (with English abstract, 13 pages).

Morita, Hiroyoshi et al., "Measurement of 3-D Objects by Means of Multi Values M—Array Patten Projection Method," Transactions of Information Processing Society of Japan, Japan, Information Processing Society of Japan, May 15, 1990, vol. 31, No. 5, pp. 683-691. (12 pages).

Office Action dated Jan. 31, 2020, for Japanese Patent Application No. 2018-560084. (with English translation, 10 pages).

* cited by examiner

SYSTEM AND METHOD FOR 3D SCENE RECONSTRUCTION WITH DUAL COMPLEMENTARY PATTERN ILLUMINATION

PRIORITY

The present patent application is a continuation of U.S. application Ser. No. 15/487,114, filed on Apr. 13, 2017, which claims priority to and incorporates by reference the corresponding provisional patent application Ser. No. 62/344,789, titled, "System and Method for 3D Scene Reconstruction with Dual Complementary Pattern Illumination" filed on Jun. 2, 2016.

TECHNICAL FIELD

This disclosure relates generally to digital imaging, and in particular but not exclusively, relates to three-dimensional scene reconstruction.

BACKGROUND INFORMATION

When a camera captures an image, a two-dimensional (2D) representation of the scene in the field of view of the camera is obtained. However, for many applications, a three-dimensional (3D) reconstruction of the scene is desired. A 3D reconstruction can be obtained by illuminating the scene with a known pattern and taking a photograph of the illuminated scene with the camera. When the point-to-point correspondence of the photograph with the known illumination pattern can be determined, triangulation can be used to determine the depth of each point, and the scene can be reconstructed in three dimensions. The correspondence problem, however, is difficult. With current solutions, there is high latency in image acquisition because many images must be taken, there is a high latency in computation of the correspondence between the multiple images, and/or there is uncertainty in determining the correspondence.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Figure 1:
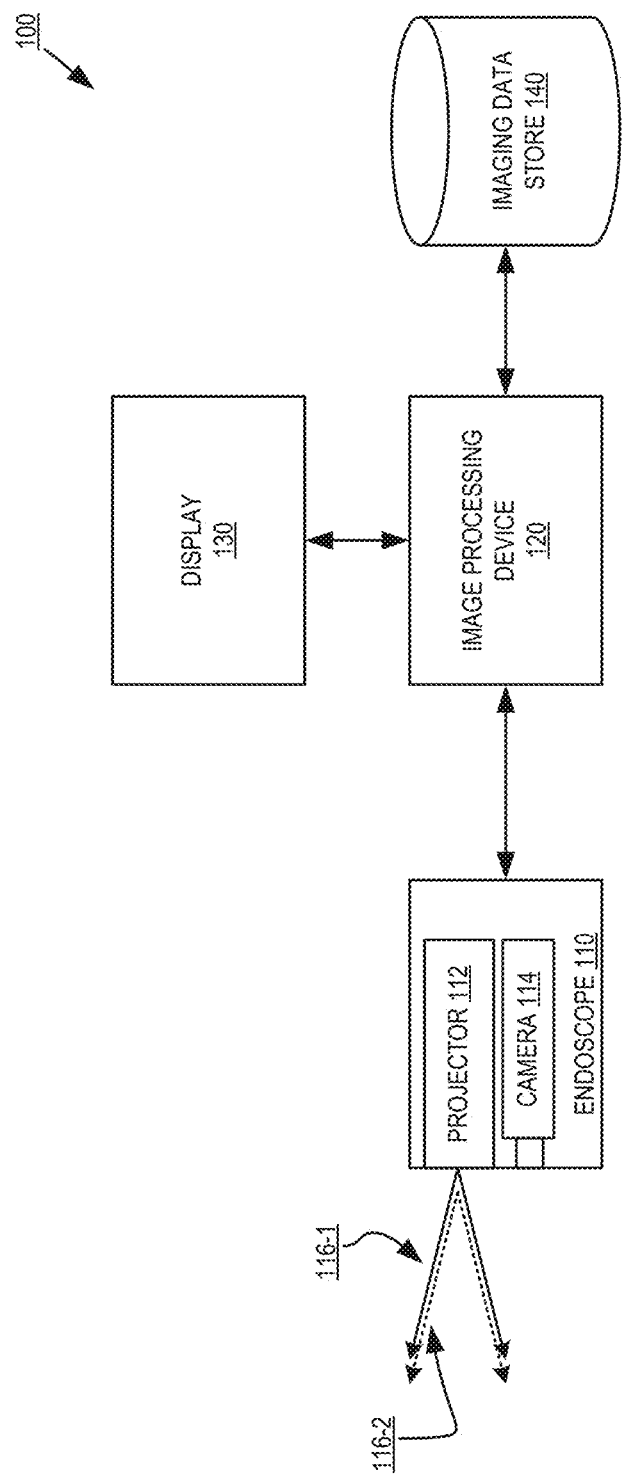
FIG. 1 is a block diagram of an exemplary system architecture for three-dimensional scene reconstruction based on dual complementary pattern illumination of the scene.

Embodiments of an apparatus, system, and process for utilizing dual complementary pattern illumination of a scene when performing depth reconstruction of the scene are described herein. In embodiments, correspondence in structured illumination with low latency and very high accuracy can be obtained using dual complementary pattern illumination of a scene, as discussed in greater detail below. In the following description, numerous details are set forth. It will be apparent, however, to one of ordinary skill in the art having the benefit of this disclosure, that the present invention may be practiced without these specific details. In some instances, well-known structures and devices are shown in block diagram form, rather than in detail, in order to avoid obscuring the present invention.

Some portions of the detailed description that follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "projecting", "capturing", "identifying", "performing", "generating", "constructing", "calibrating", "performing", "tracking", or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

The present invention also relates to an apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions.

The algorithms and displays presented herein are not inherently related to any particular computer or other apparatus. Various general purpose systems may be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the invention as described herein.

FIG. 1 is a block diagram of an exemplary system architecture 100 for three-dimensional scene reconstruction based on dual complementary pattern illumination of the scene. In one embodiment, the system includes an endoscope 110 communicably coupled with an image processing device 120. In embodiments, endoscope 110 may be coupled via physical connection (e.g., wired connection), via a wireless connection (e.g., wireless network, near field communication, etc.), or other type of communications link. Furthermore, the imaging processing device 120 may be communicably coupled with a display 130 and an imaging data store 140, over any of the communications links discussed herein.

Endoscope 110 is responsible for capturing images of a scene with camera 114. Camera 114 may include a lens and an image sensor. In one embodiment, the camera 114 includes a single lens and a single image sensor, although multiple lens and/or image sensor cameras could be used consistent with the discussion herein. The lens of camera 114 allows light to pass from outside of endoscope 110 (e.g., a scene) to the image sensor of camera 114. The image sensor, such as a complementary metal-oxide-semiconductor (CMOS) image sensor, charge-coupled device (CCD) image sensor, etc., captures the light on a grid of pixels and conveys image information to image processing device 120.

Image processing device 120 is a computer processing system, such as a desktop computer, laptop computer, tablet computer, mobile telephone, or purpose build computing device, which includes a processor, memory, communication interfaces, and other components typically found in computer processing systems. One embodiment of a computing processing system is discussed in greater detail below in FIG. 10. In one embodiment, image processing device 120 receives image data captured by camera of endoscope, which can be displayed on display 130 and/or stored in an imaging data store 140. For example, display 130 may display captured image data to a doctor, nurse, or other diagnostician that is analyzing image data captured by endoscope 110. Furthermore, imaging data store 140 may store captured image data for later analysis by a health care professional, such as storing captured pre-surgery image data or storing image data to a patient's electronic medical records.

In one embodiment, endoscope 110 enables image processing device 120 to perform 3D scene reconstruction of captured image data using dual complementary patterns projected onto a scene being imaged. Endoscope 110 includes projector 112 for projecting a first reference image 116-1 and a second reference image 116-2, which are captured by camera 114 and provided to image processing device 120. In one embodiment, projector 112 is a digital micromirror device (DMD) with projection optics and a light source (not shown). The DMD is a matrix of micromirrors that can be controlled by image processing device 120 such that each micromirror can either reflect light towards a scene, or away from it. The light source shines on the DMD, and the pattern on the DMD goes through the projection optics and is projected onto the scene. In one embodiment, the light source can be a laser of specific frequency to differentiate its illumination from ambient illumination (if any).

Figure 4A:
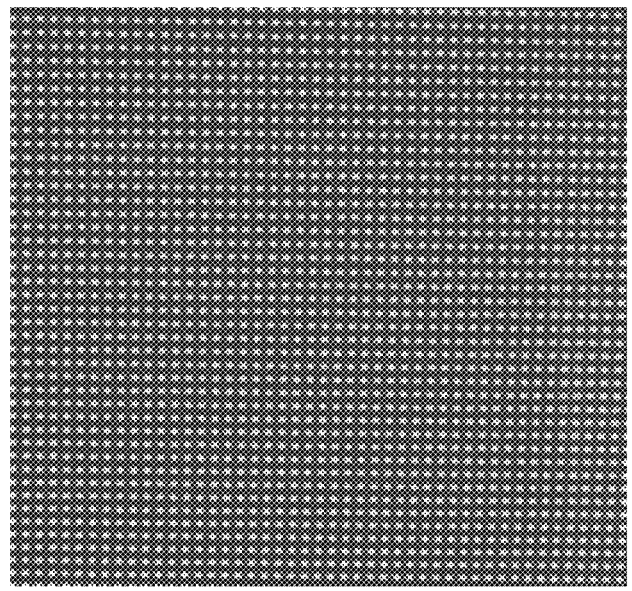
FIG. 4A illustrates one embodiment of a first reference image for use in three-dimensional scene reconstruction.
Figure 4B:
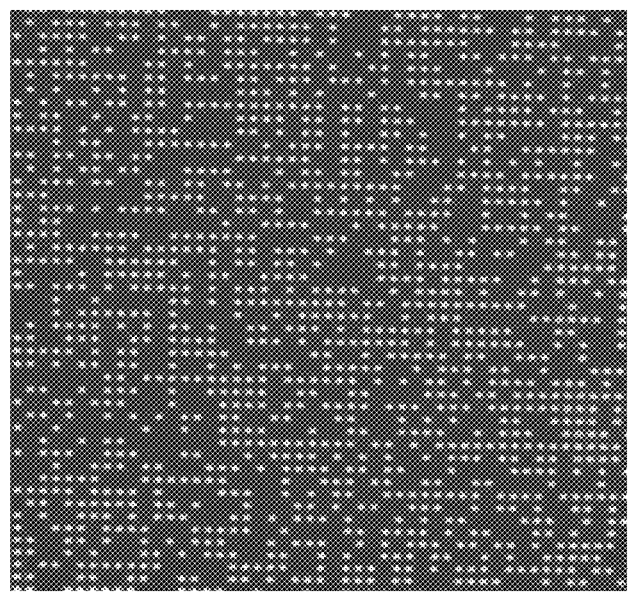
FIG. 4B illustrates one embodiment of a second complementary reference image for use in three-dimensional scene reconstruction.

In one embodiment, image processing device 120 controls projector 112 and camera 114 to project a first reference image 116-1, such as a full grid of dots from the DMD micromirrors, which is captured by camera 114. Then, a second reference image 116-2, such as the same grid of dots but with randomly selected dots missing (e.g., a dropped dots grid pattern), is projected by projector 112 and another image is captured by camera 114. One embodiment of a full grid of dots reference image is illustrated in FIG. 4A, while a complementary dropped dots grid pattern is illustrated in FIG. 4B. In another embodiment, the first reference image may be a first subset of the full grid of dots illustrated in FIG. 4A, while the second reference image is a second subset of the full grid of dots, where the first and second subsets collectively include each of the full grid of dots. Different reference images can be used as reference images consistent with the discussion herein, so long as each of the dots can be identified from the dual complementary patterns.

In one embodiment, the projector 112 is controlled by image processing device 120 to display the dual complementary reference images on a scene, with each reference image being a reference image stored in a memory of image processing device 120. After the images of the dual complementary reference images (e.g., 116-1 and 116-2) are acquired by camera 114, image processing device 120 utilizes the captured images of the two reference images projected on the scene to quickly and accurately perform 3D scene reconstruction.

Figure 6:
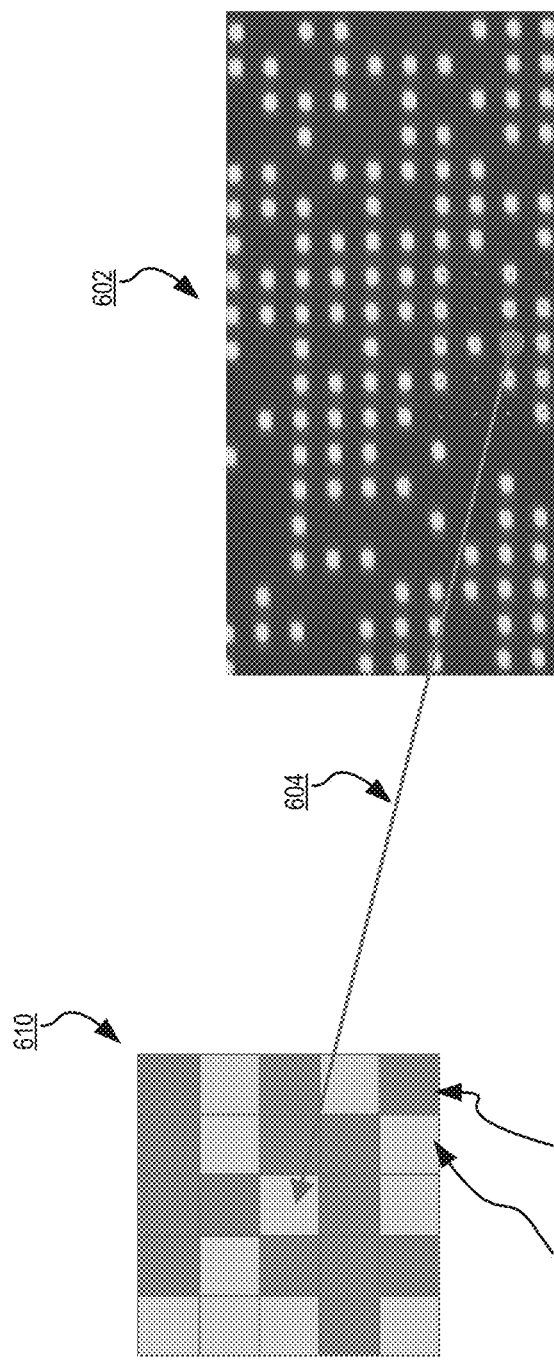
FIG. 6 illustrates one embodiment of feature vector generation using dual complementary pattern illumination.

In one embodiment, 3D scene reconstruction is enabled by image processing device 120 assigning every dot in the full dot grid pattern, e.g., reference image 116-1, a feature representation based on the second, complementary reference image 116-2. In one embodiment, this feature representation consists of a feature vector having a length that is a given number of nearest-neighbor dots. FIG. 6 illustrates one embodiment of neighbor detection for generation of the feature vector. As illustrated in FIG. 6, the complementary, second projection pattern with randomly dropped dots is illustrated 602. For a given dot 604 in the second reference image 602, a certain number of neighboring dots 610, such as all dots one dot away, two dots away, three dots away, as well as dots in other preconfigured patterns, are determined as either being present or not present in the second reference image 602. In one embodiment, the feature vector represents which neighbor dots are present and not present in the second, complementary second reference image 602. For each neighbor dot represented in the feature vector, a 0 is stored for a dot that is missing in the missing dot grid pattern (e.g., 616), and 1 is stored for a dot that exists in the missing dot grid pattern (e.g., 612). A feature vector is constructed by image processing device 120 for each dot in the first, full gird of dots reference image. For example, the feature vector for dot 604 can be expressed as the one-dimensional binary array: [0,1,1,1,1,0,0,1,0,0, 0, 1,1,1,1,1,1,0,0,1,0,0,1].

When the two nearest neighbor dots of each dot are used to generate the feature vector, there may be $2^{24}$ distinct feature vectors possible for identifying each dot in a full grid of dots reference image (e.g., there are $2^N$ distinct feature vectors possible for dots in the first reference image when N nearest neighbor dots are used and 50% of the dots are randomly dropped from the second, complementary reference image). Therefore, an extremely low probably of false match is attained when a sufficient number of dots, such as 50%, are randomly dropped in the second reference image and when a sufficient number of nearest neighbor dots are used for generating feature vectors. From the feature vector for each dot, the corresponding dot on the reference full dot grid pattern can be established. That is, the feature vector acts as a unique identifier for each dot in the first reference image using image data captured of the second, complementary reference image. Once the dots within captured image data of the first, full grid of dots reference image is identified using the feature vectors constructed from dots captured in a second, dropped dots reference image, depth reconstruction can be performed on captured image data.

Returning to FIG. 1, in one embodiment, image processing device 120 utilizes calibrated depth and pixel coordinate dictionaries that relates how the image sensor of camera 114 picks up the dots on an image sensor pixel array with real world depth and coordinate values. Using calibration data, as described in greater detail below, the pixel coordinates of each dot on an image sensor can be translated to a 3D position in the real world. That is, how the image sensor of camera 114 picks up a dot on an image sensor array may be converted to real-world depth and real world coordinate values to provide real world (x, y, z) coordinates for captured image data. Thus, translating each dot in the full dot grid pattern to real world 3D coordinates yields a 3D scene reconstruction.

Although an endoscope is illustrated and discussed, 3D scene reconstruction using dual complementary pattern illumination need not be limited to endoscopes. Other imaging devices that perform imaging and would benefit from 3D information, such as mobile phones, robotic devices, computer vision systems, autonomous vehicles, self-driving vehicles, etc., can implement the methods and systems discussed herein. These devices will also benefit from the fast and accurate 3D scene reconstruction discussed herein.

Figure 2:
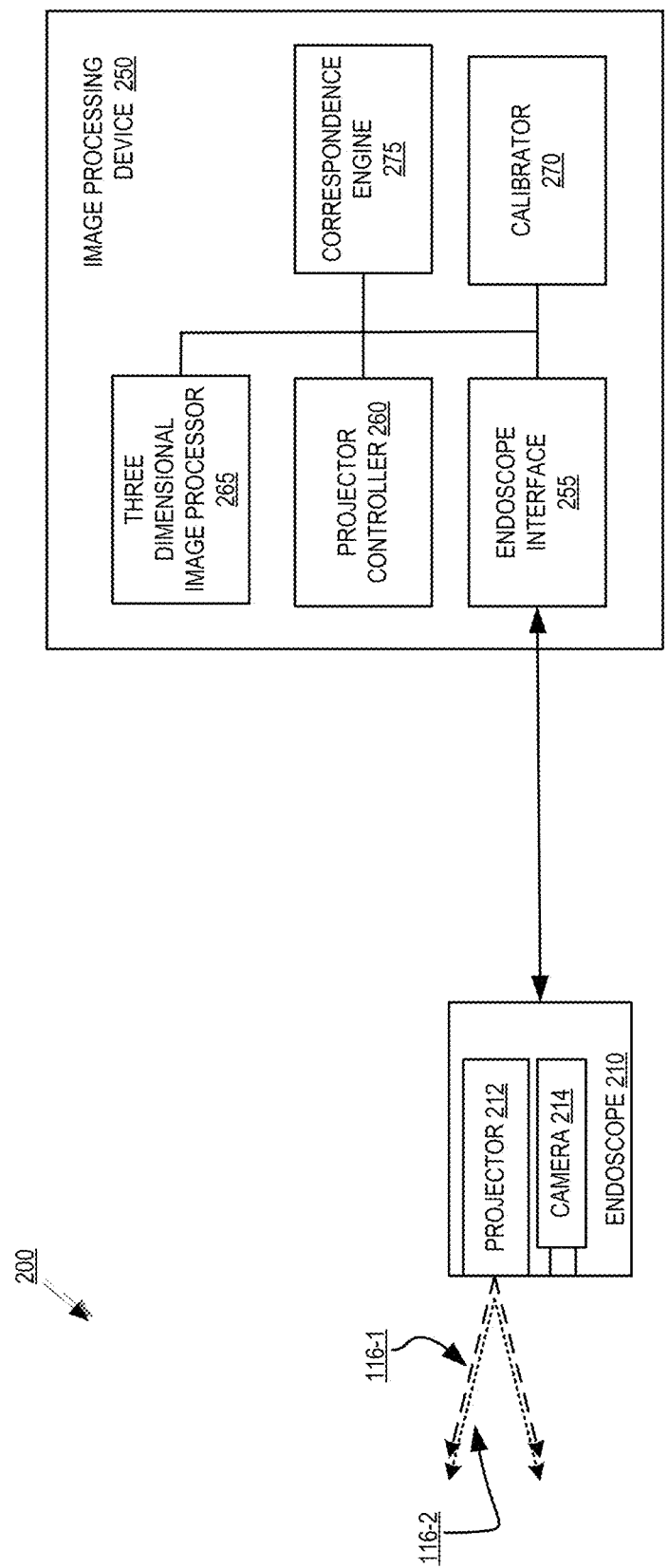
FIG. 2 is a block diagram of one embodiment of an endoscope and an image processing device.

FIG. 2 is a block diagram of one embodiment 200 of an endoscope 210 and an image processing device 250. Endoscope 210 and an image processing device 250 provide additional details for the endoscope 110 and image processing device 120 discussed above.

In one embodiment, the image processing device 250 includes an endoscope interface 255, a projector controller 260, a three dimensional image processor 265, a correspondence engine 275, and a calibrator 270. The endoscope 210 includes a projector 212, such as a DMD projection device, and a camera 214. In one embodiment, the endoscope 210 and image processing device 250 communicate with each other over a wired or wireless communications link, as discussed above in FIG. 1.

The image processing device 250, in embodiments, can be implemented in a computing device, such as a desktop computer, laptop computer, tablet computer, computing appliance, video game console, mobile telephone, as well as other computing devices. Endoscope interface 255 is responsible for communicably coupling image processing device 250 with endoscope 210 to enable image processing device 250 the ability to control the projector 212 of endoscope 210, as well as to receive image data captured by camera 214 of endoscope 210.

In one embodiment, projector controller 260 is responsible for controlling the projector 212 of endoscope. In one embodiment, projector 212 is a DMD device with individually controllable micromirrors that can reflect a light source on a scene. In one embodiment, projector controller 260 configures projector 212 to display dual complementary reference images 216-1 and 216-2. In one embodiment, the first reference image 216-1 projects a full grid of dots (e.g., each of the dots corresponding to mirrors of a DMD projection device). Three dimensional image processor 265 controls camera 214 to capture an image of a scene having the first reference image 216-1 projected thereon. Then, projector controller 260 configures projector 212 to project a second reference image 216-2 on a scene, where the second reference image is complementary to the first reference image, but has missing dots. In one embodiment, a sufficient number of dots are randomly selected for display in the reference image 216-1 to ensure that each dot in the first reference image 216-1 can be accurately identified. In one embodiment, 50% of the dots are randomly selected for display in reference image 216-2, and the second reference image 216-2 is stored in a memory of image processing device 250 for later re-use during additional dual complementary reference image projections for 3D scene reconstruction.

After images of the scene upon which the first and second reference images are projected have been captured, correspondence engine 275 is responsible for identifying dots in the first reference image 216-1 based on the complementary nature of the second reference image 216-2. As discussed herein, in one embodiment, correspondence engine 275 utilizes a feature vector for each dot of the first reference image 216-1 generated from nearest neighbors of the second reference image 216-2. The feature vector for each dot defines an identifier for each dot in the full grid of dots of the first reference image 216-1 with sufficient accuracy to ensure proper identification of individual dots projected on a scene. In one embodiment, the feature vectors can be generated by correspondence engine 275 from the second reference image 216-2 prior to projection on a scene and image capture by endoscope 210. In one embodiment, the correspondence engine 275 analyzes a captured image of a scene with the first reference image 216-1 projected thereon, and a captured image of a scene with the second reference image 216-2 projected thereon. From the second reference image 216-2 projected on the scene, the correspondence engine 275 generates feature vector s for each dot projected on the scene in the first reference image. That is, a dot from the first, full grid of dots from a first captured image data is associated with the dot (or lack of a dot) in the second captured image data having the corresponding position in the capture image data. Then, a comparison of the feature vectors generated from the second reference image 216-2 in the captured image data with the feature vectors generated before image capture, enables correspondence engine 275 to directly and efficiently identify each dot in the image data of the first reference image 216-1 projected on the scene.

In one embodiment, after each dot has been identified in the captured image data, pixel coordinates are determined by three-dimensional image processor 265 for each dot in the full grid of dots. Pixel coordinates, as discussed herein, refer to what pixel(s) on the image sensor of camera 214 the dot was captured. In one embodiment, more than one pixel may pick up a dot projected on a scene, and thus three-dimensional image processor 265 determines a centroid of each projected dot. The determined pixel coordinates for each dot may then be translated, using calibrated depth and coordinate dictionaries relating pixel coordinates to real world depth and x-y values. In one embodiment, the depth and coordinate dictionaries are generated by calibrator 270, as discussed in greater detail below in FIGS. 7, 8A, and 8B. In one embodiment, given a determined pixel coordinate, three-dimensional image processor 265 determines a depth value (z) of the scene at the point upon which the pixel was projected as a function of the pixel coordinate. Furthermore, once the depth value is known, three-dimensional image processor 265 may further determine real world coordinates values (x, y) of the scene at the point upon which the pixel was projected. From these two calculations, real world coordinates are determined for the point in the captured image data, thereby associating real world (x, y, z) values with that point. When the real-world coordinates are determined for each projected point from the first reference image, the collection of real world coordinate and depth values is used to perform 3D scene reconstruction on the captured image.

In embodiments, projection of the dual complementary patterns, capture of image data, and correspondence determination may be performed rapidly and accurately by image processing device 250. Similarly, determination of pixel coordinates and translation of those pixel coordinates to real world (x, y, z) values may also be performed rapidly and accurately. As a result, 3D data for captured images may be generated in real time, or near real time, as one or more images are captured. Furthermore, the rapid and accurate 3D scene reconstruction process enables 3D scene reconstruction of live video data, as well as 3D scene reconstruction of captured still images.

After 3D scene reconstruction of captured image data has been performed by three dimensional image processor 265, three-dimensional image processor 265 may send the 3D image data to storage and/or a display unit (not shown). For example, images of a 3D reconstructed scene may be stored and tagged in a pre-operative image registry. As another example, real-time 3D reconstructed image data may be output to a display device to enable a medical professional to view the 3D image data.

Figure 3:
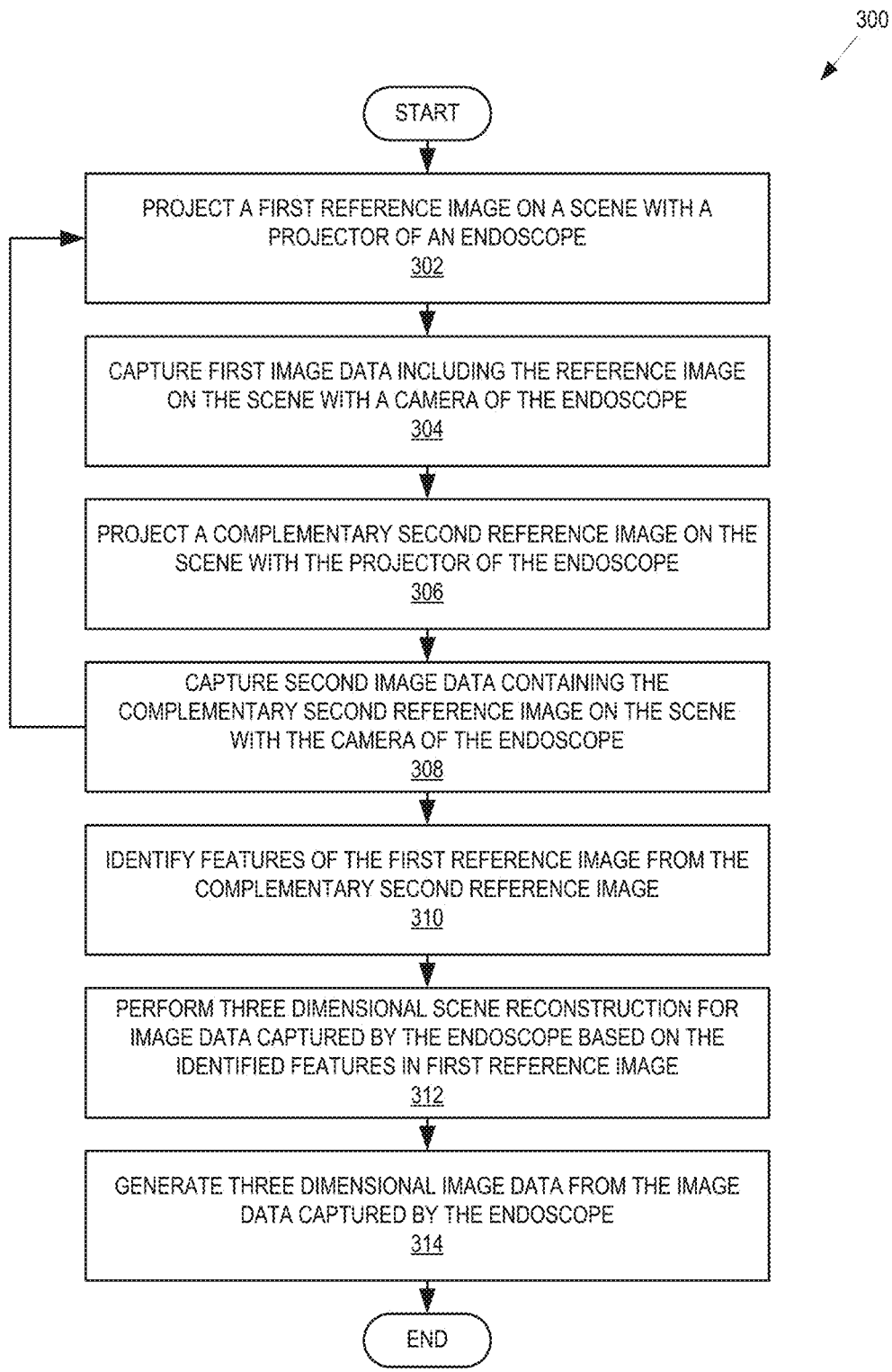
FIG. 3 is a flow chart illustrating a process for performing three-dimensional scene reconstruction by projecting complementary patterns on the scene.

FIG. 3 is a flow chart illustrating a process 300 for performing three-dimensional scene reconstruction by projecting complementary patterns on the scene. The process is performed by processing logic that may comprise hardware (circuitry, dedicated logic, etc.), software (such as is run on a general purpose computer system or a dedicated machine), firmware, or a combination. In one embodiment, the process is performed by an endoscope and an image processing device (e.g., endoscope 110 or 210, and image processing device 120 or 250).

Referring to FIG. 3, processing logic begins by projecting a first reference image on a scene with a projector of an endoscope (processing block 302). In one embodiment, the first reference image is a grid of dots in a first pattern, such as the full grid of dots illustrated in FIG. 4A. The projected pattern may be projected with an infrared, or other light emitting device, capable of projecting different patterns. One such device, as discussed herein, is a DMD projection device. Processing logic then captures first image data including the reference image on the scene with a camera of the endoscope (processing block 304).

Processing logic projects a complementary second reference image on the scene with the projector of endoscope (processing block 306). In one embodiment, the second reference image is a grid of dots with a portion of dots randomly dropped from the full grid pattern. An example of a dropped dots pattern is illustrated in FIG. 4B. In one embodiment, a sufficient number of dots, such as 40%, 50%, 60%, etc., are randomly dropped to ensure that each dot may be uniquely identified using a feature vector, as discussed herein. Processing logic then captures second image data containing the complementary second reference image on the scene with the camera of the endoscope (processing block 308).

In embodiments, the order of projecting and capturing first and second reference images may be changed so that the complementary pattern is projected prior to a full grid of dots pattern. In either embodiment, the process may return to processing block 302 to capture additional dual complementary reference images projected on a scene.

Processing logic identifies features of the first reference image from the complementary second reference image (processing block 310). In one embodiment, features of the first reference image, such as dots in a grid of dots, are identified using features of the complementary second reference image. In one embodiment, discussed in greater detail in FIG. 5, a feature vector is constructed from the second reference image as an identifier for each feature of the first reference image. Then, using the captured images of processing blocks 304 and 308, the feature vectors for reference images projected on a scene may be generated from the image captured in processing block 308, and corresponding dots identified by matching the constructed and generated feature vectors.

After identification of features in the first reference image, processing logic performs three dimensional scene reconstruction for image data captured by the endoscope based on the identified features in the first reference image (processing block 312). Processing logic generates depth and real world coordinate values (e.g., real world x, y, and z data) for portions of image data corresponding to those portions upon which a dot was projected. Using the collection of real world coordinate values, processing logic can generate three dimensional image data from the image data captured by endoscope (processing block 314). In embodiments, the generated three dimensional image data may be outputted, by processing logic, to a display (e.g., a display communicably coupled with processing logic), a data store (e.g., a pre-operative image data store, a patient record, etc.), or other output.

Figure 5:
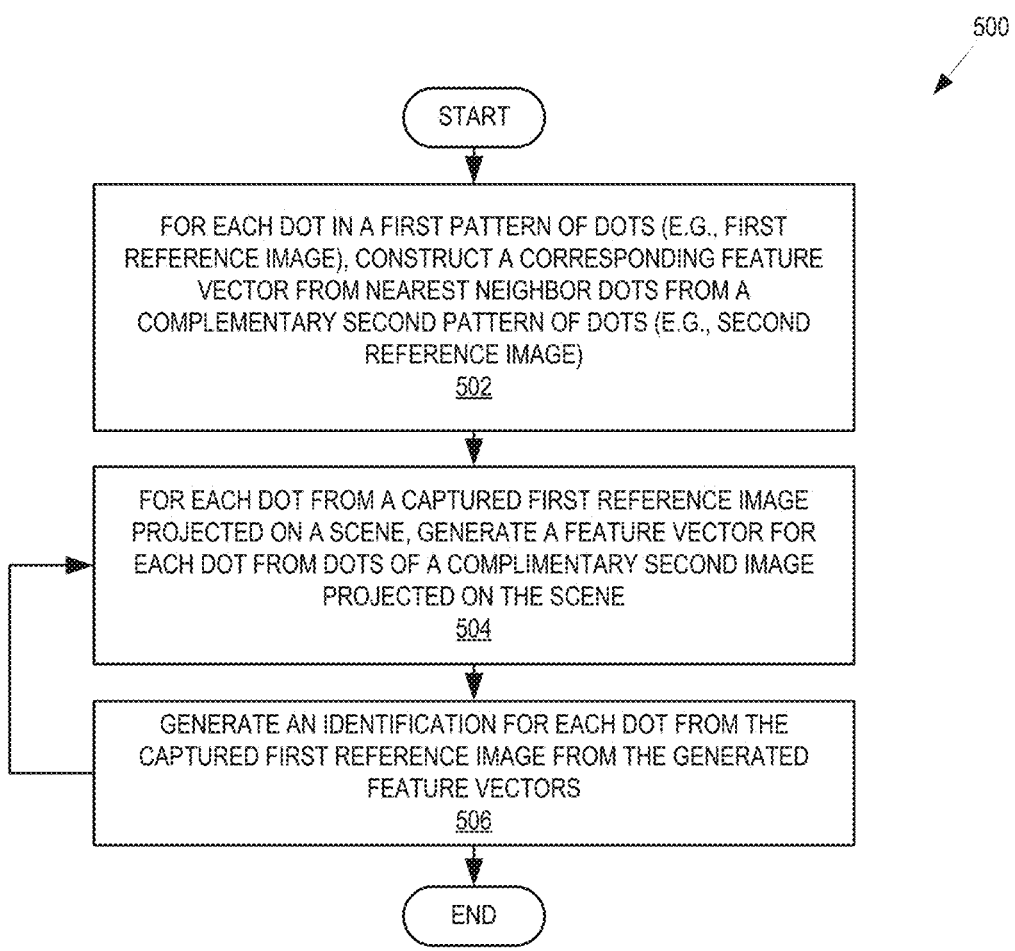
FIG. 5 is a flow chart illustrating a process for using complementary patterns projected on a scene during three-dimensional scene reconstruction.

FIG. 5 is a flow chart illustrating a process 500 for using complementary patterns projected on a scene during three-dimensional scene reconstruction. The process is performed by processing logic that may comprise hardware (circuitry, dedicated logic, etc.), software (such as is run on a general purpose computer system or a dedicated machine), firmware, or a combination. In one embodiment, the process is performed by an endoscope and an image processing device (e.g., endoscope 110 or 210, and image processing device 120 or 250).

Referring to FIG. 5, processing logic begins by, for each dot in a first pattern of dots (e.g., a first reference image), constructing a corresponding feature vector from nearest neighbor dots from a complementary second pattern of dots (e.g., a complementary second reference image) (processing block 502). FIG. 6 illustrates a dot 604 in the complementary second pattern of dots 602. The feature vector corresponding to the nearest neighbors may indicate which neighboring dots are projected and which are not (e.g., lack of a dot 616). The grid of neighboring dots 610 illustrates which dots, within two dots of a dot of interest, are projected (e.g., dot 612), and which are not (e.g., lack of a dot 616). A feature vector, such as the binary array [0,1,1,1,1,0,0,1,0,0,0,1,1,1, 1,1,1,1,0,0,1,0,0,1], therefore describes the nearest neighbors of dot 604, with a 1 indicating the dot exists and 0 indicating the dot does not exist. In an embodiment where 50% of the dots are randomly dropped in the complementary second reference image, there are $2^{24}$ distinct possible features vectors, which ensures an extremely low probability of false match. The feature vectors constructed for each dot in the first pattern of dots may then be stored for later use in identifying features of reference images.

In one embodiment, the feature vectors are constructed prior to 3D scene reconstruction. Then, during scene reconstruction, for each dot from a captured first reference image projected on a scene, processing logic generates a feature vector for each dot from dots of a complementary second image projected on the scene (processing block 504). That is, during 3D scene reconstruction, first and second reference images are projected on a scene, images captured of the reference images, and feature vectors generated in accordance with the process of processing block 502. Processing logic uses the feature vectors to generate an identification for each dot from the captured first reference image (processing block 506).

As discussed herein, once each dot is identified in the first reference image, real world depth and coordinate values may be determined for each dot using calibrated depth and coordinate dictionaries. These dictionaries enable a translation from pixel coordinates of the dots in captured image data to real world 3D coordinates. The translations in the depth and coordinate dictionaries for each pixel are generated during calibration of an imaging device, such as endoscope 110 or 210.

Figure 7:
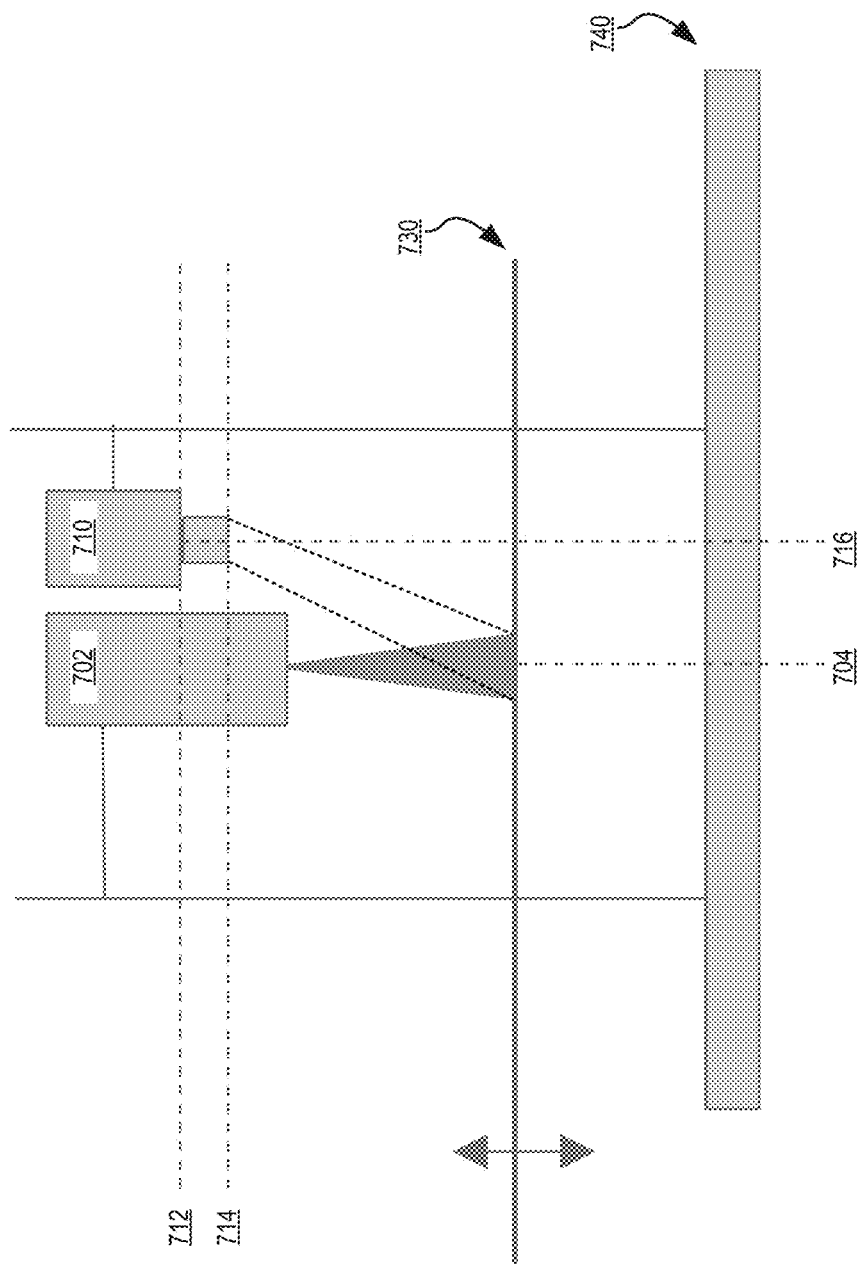
FIG. 7 is a block diagram of one embodiment of a system for calibrating an imaging device that uses dual complementary patterns for illuminating a scene.

FIG. 7 is a block diagram of one embodiment of a system 700 for calibrating an imaging device that uses dual complementary patterns for illuminating a scene. The system includes a projector 702 and a camera 710, such as those discussed in FIGS. 1 and 2. Furthermore, a moveable stage 730 is also provided on a perpendicular plane to the plane of projection and image capture. In one embodiment, the moveable stage 730 is coupled with a support 740 (e.g., a breadboard) and may be adjusted known distances towards and away from the plane 712 of an image sensor, and a plane 714 of a lens, of camera 710.

In one embodiment, the moveable stage 730 may be moved perpendicular to the camera 710 and projector 702 to establish a known distance between a projection surface of moveable stage 730 (upon which projector 702 projects reference images) and camera 710. Projector 702 may then project the dual complementary reference images discussed herein, which are captured by camera 710. Using the processes of FIGS. 8A and 8B discussed below, an image processing device calibrates dictionaries for translating pixel coordinates (e.g., sensor pixel coordinate data) for captured reference images to real world coordinate values. The process of calibration is performed at a plurality of depth planes ($z_i$), such as every 1 mm of an intended range of use of an imaging device. Then a linear regression analysis may be performed to model the captured pixel coordinates to real-world depth and pixel values. These models are stored, for each dot in a, full grid of dots reference image, in the depth and coordinate dictionaries discussed in greater detail below.

Figure 8A:
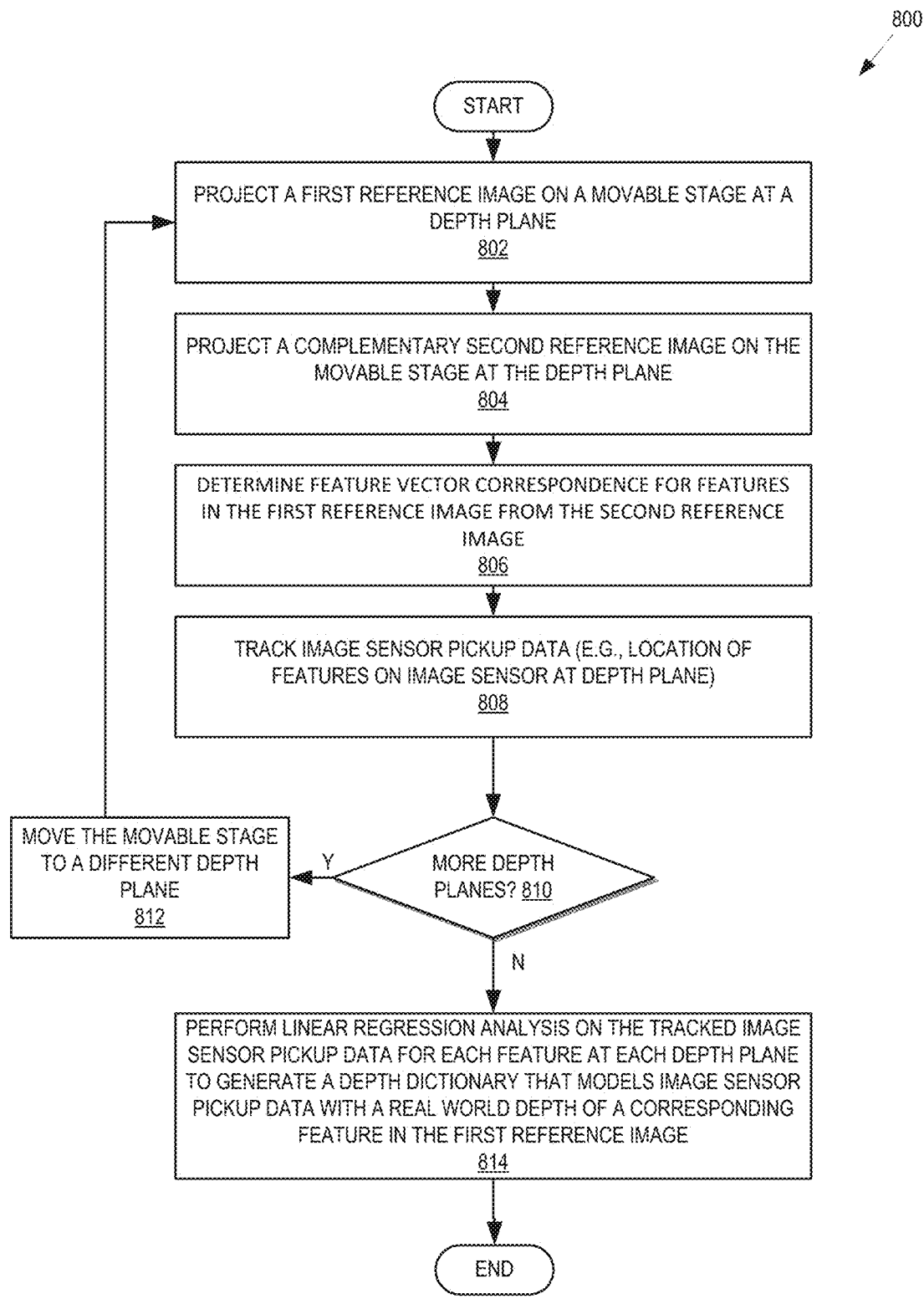
FIG. 8A is a flow chart illustrating a process for performing depth calibration of an imaging device that utilizes dual complementary patterns for illuminating a scene.

FIG. 8A is a flow chart illustrating a process 800 for performing depth calibration of an imaging device that utilizes dual complementary patterns for illuminating a scene. The process is performed by processing logic that may comprise hardware (circuitry, dedicated logic, etc.), software (such as is run on a general purpose computer system or a dedicated machine), firmware, or a combination. In one embodiment, the process is performed by a calibrator of an image processing device (e.g., calibrator 270) in conjunction with a calibration system (e.g., system 700).

Referring to FIG. 8A, processing logic begins by projecting a first reference image on a movable stage at a depth plane (processing block 802). In one embodiment, the depth plane is a known distance between the image sensor of a camera and the surface of the moveable stage. As discussed herein, the first reference image may be a grid of dots projected by a DMD projection device. Furthermore, the grid of dots may be a full grid of dots, such as that illustrated in FIG. 4A.

Processing logic projects a complementary second reference image on the moveable stage at the depth plane (processing block 804). In one embodiment, the complementary second reference image is a second grid of dots with randomly dropped dots, such as that illustrated in FIG. 4B.

Processing logic determines a feature vector correspondence for features in the first reference image from the second reference image (processing block 806). In one embodiment, the correspondence between features of the first and second reference images is determined according to the process of FIG. 5 discussed above.

Processing logic tracks image sensor pickup data, such as the location of features on an image sensor at a depth plane (processing block 808). In one embodiment, the tracking by processing logic includes processing logic capturing image sensor pixel coordinates for each feature (e.g., dot) of the first reference image. In one embodiment, where more than one pixel of an image sensor picks up a feature, the centroid of the pixels capturing the feature is used as the pixel coordinate at the depth plane.

When there are additional depth planes for calibration (processing block 810), processing logic moves the moveable stage to a different depth plane (processing block 812). The projection and capture of the reference images, and tracking of image sensor pickup data, is repeated for a plurality of depth planes. In one embodiment, the plurality of depth planes includes a range of depth planes corresponding to an intended range of use of the imaging device being calibrated. For example, the depth planes may range from 0.25 mm to 20 mm in depth, and the moveable stage may be moved at 0.25 mm increments within this range. Other ranges of field of use, as well as incremental movement distances of depth planes, may be used in accordance with the discussion herein.

When there are no additional depth places for calibration (processing block 810), processing logic performs regression analysis on the tracked image sensor pickup data for each feature vector at each depth plane to generate a depth dictionary that models image sensor pickup data with a real world depth of a corresponding feature in the first reference image (processing block 814). In one embodiment, the depth dictionary provides, for each feature (e.g., dot) of the first reference image, a function that translates pixel coordinates captured for that feature to a real world depth (z) of the feature in the scene in which the feature is projected.

Figure 8B:
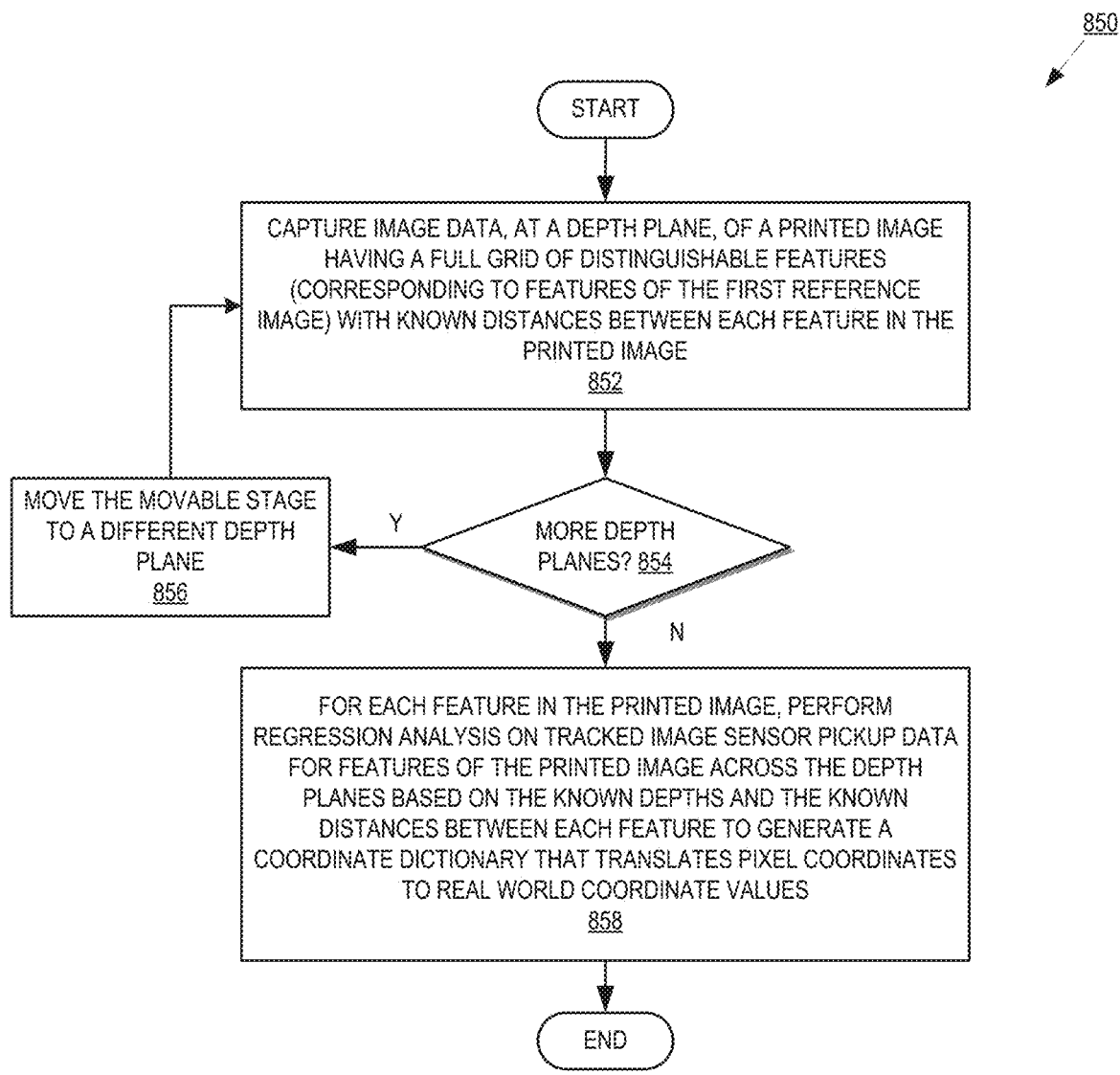
FIG. 8B is a flow chart illustrating a process for performing coordinate calibration of an imaging device that utilizes dual complementary patterns for illuminating a scene.

FIG. 8B is a flow chart illustrating a process 850 for performing coordinate calibration of an imaging device that utilizes dual complementary patterns for illuminating a scene. The process is performed by processing logic that may comprise hardware (circuitry, dedicated logic, etc.), software (such as is run on a general purpose computer system or a dedicated machine), firmware, or a combination. In one embodiment, the process is performed by a calibrator of an image processing device (e.g., calibrator 270) in conjunction with a calibration system (e.g., system 700).

Referring to FIG. 8B, processing logic begins by capturing image data, at a depth plane, of a printed image having a full grid of distinguishable features, which correspond to the features of a first reference image, with known distances between each feature in the printed image (processing block 852). In one embodiment, the printed image has dots with known distances between each dot, and which corresponds to a full grid of dots pattern in a first reference image. Furthermore, the features in the printed image are distinguishable in the captured image data, such as distinguishable by color, intensity, shape, etc.

When there are additional depth planes for capturing the printed image for calibration (processing block 854), processing logic moves the movable stage to a different depth plane (processing block 856). In one embodiment, the depth planes are the same as those used in the calibration discussed in FIG. 8A. However, in embodiments, different depth planes over an intended range of use of an imaging device could be used.

When there are no additional depth planes for capturing the printed image for calibration (processing block 854), processing logic performs, for each feature in the printed image, regression analysis on tracked image sensor pickup data for features of the printed image across the depth planes based on the known depths and the known distances between each feature to generate a coordinate dictionary that translates pixel coordinates to real world coordinate values (processing block 858). In one embodiment, the coordinate dictionary is, for each feature (e.g., dot) of a reference image, a model that translates pixel coordinate values and a known depth (obtained according to the process of FIG. 8A) to real world coordinate values (e.g., real world x, y values) for a feature projected on a scene by an imaging device. The image sensor pixel coordinate data, along with the known depth data, enables processing logic to perform a displacement calculation between the features in the printed image in the image plane.

In embodiments, the processes of FIGS. 8A and 8B can be performed for individual imaging devices to provide a calibration process that accounts for manufacturing differences between devices. That is, even if different devices are built to strict tolerances, minor imperfections in lens, sensor, projector, distances there between, etc. can alter the ultimate results of depth reconstruction. Thus, the calibration of FIGS. 8A and 8B ensure that each device is properly calibrated to ensure fast and accurate depth reconstruction of image data using the calibrated depth and coordinate dictionaries, when used with the dual complementary reference images discussed herein.

Figure 9:
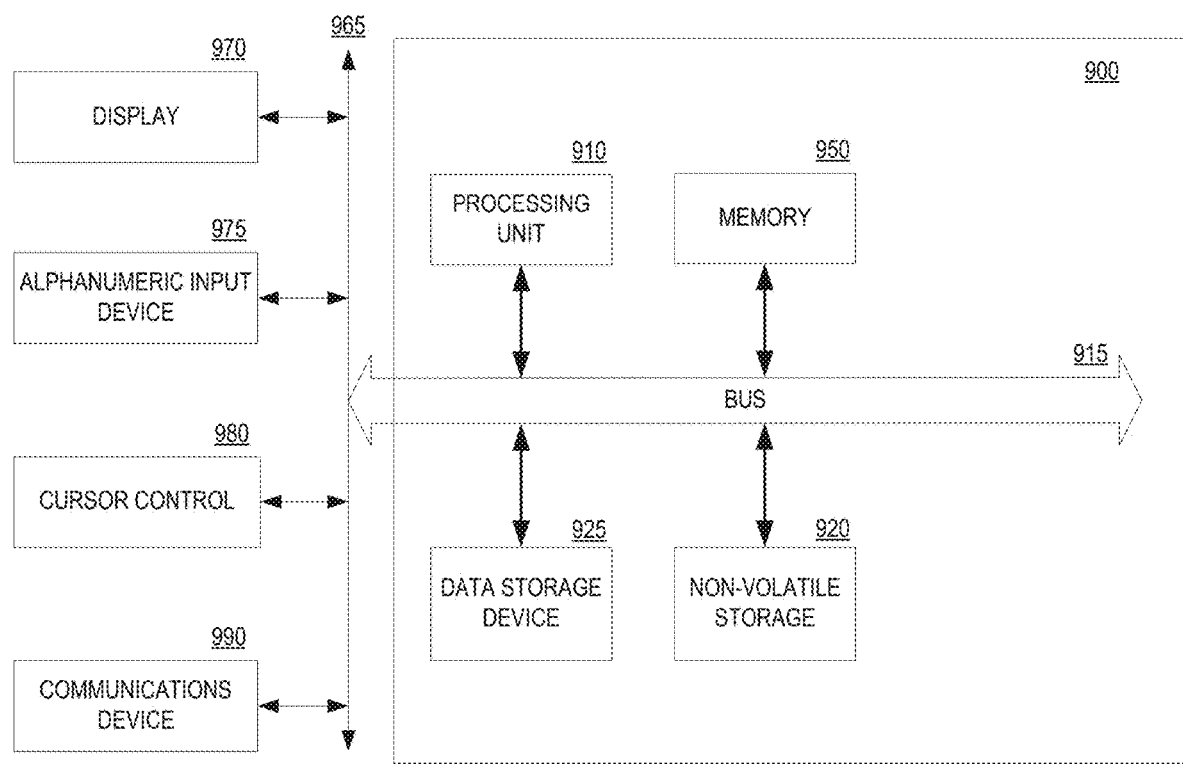
FIG. 9 is one embodiment of a computer system that may be used with the present invention

FIG. 9 is one embodiment of a computer system that may be used with the present invention. The computer system may provide the functionality of the image processing systems discussed above. Furthermore, it will be apparent to those of ordinary skill in the art, however, that other alternative systems of various system architectures may also be used.

The computer system illustrated in FIG. 9 includes a bus or other internal communication means 915 for communicating information, and a processor 910 coupled to the bus 915 for processing information. The system further comprises a random access memory (RAM) or other volatile storage device 950 (referred to as memory), coupled to bus 915 for storing information and instructions to be executed by processor 910. Memory 950 also may be used for storing temporary variables or other intermediate information during execution of instructions by processor 910. The system also comprises a read only memory (ROM) and/or static storage device 920 coupled to bus 915 for storing static information and instructions for processor 910, and a data storage device 925 such as a magnetic disk or optical disk and its corresponding disk drive. Data storage device 925 is coupled to bus 915 for storing information and instructions.

The system may further be coupled to a display device 970, such as a light emitting diode (LED) display or a liquid crystal display (LCD) coupled to bus 915 through bus 965 for displaying information to a computer user. An alphanumeric input device 975, including alphanumeric and other keys, may also be coupled to bus 915 through bus 965 for communicating information and command selections to processor 910. An additional user input device is cursor control device 980, such as a mouse, a trackball, stylus, or cursor direction keys coupled to bus 915 through bus 965 for communicating direction information and command selections to processor 910, and for controlling cursor movement on display device 970.

Another device, which may optionally be coupled to computer system 900, is a communication device 990 for accessing other nodes of a distributed system via a network. The communication device 990 may include any of a number of commercially available networking peripheral devices such as those used for coupling to an Ethernet, token ring, Internet, or wide area network. The communication device 990 may further be a null-modem connection, or any other mechanism that provides connectivity between the computer system 900 and the outside world. Note that any or all of the components of this system illustrated in FIG. 9 and associated hardware may be used in various embodiments of the present invention.

It will be appreciated by those of ordinary skill in the art that any configuration of the system may be used for various purposes according to the particular implementation. The control logic or software implementing the present invention can be stored in memory 950, data storage device 925, or other storage medium locally or remotely accessible to processor 910.

It will be apparent to those of ordinary skill in the art that the system, method, and process described herein can be implemented as software stored in memory 950 or read only memory 920 and executed by processor 910. This control logic or software may also be resident on an article of manufacture comprising a computer readable medium having computer readable program code embodied therein and being readable by the data storage device 925 and for causing the processor 910 to operate in accordance with the methods and teachings herein.

The present invention may also be embodied in a handheld or portable device containing a subset of the computer hardware components described above. For example, the handheld device may be configured to contain only the bus 915, the processor 910, and memory 950 and/or 925. The handheld device may also be configured to include a set of buttons or input signaling components with which a user may select from a set of available options. The handheld device may also be configured to include an output apparatus such as a liquid crystal display (LCD) or display element matrix for displaying information to a user of the handheld device. Conventional methods may be used to implement such a handheld device. The implementation of the present invention for such a device would be apparent to one of ordinary skill in the art given the disclosure of the present invention as provided herein.

The present invention may also be embodied in a special purpose appliance including a subset of the computer hardware components described above. For example, the appliance may include a processor 910, a data storage device 925, a bus 915, and memory 950, and only rudimentary communications mechanisms, such as a small touch-screen that permits the user to communicate in a basic manner with the device. In general, the more special-purpose the device is, the fewer of the elements need be present for the device to function.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method comprising:
    projecting, with a projector of an imaging device, a first reference image and a complementary second reference image on a scene;
    capturing, with a camera of the imaging device, first image data and second image data including the first reference image and the complementary second reference image on the scene;
    identifying features, with a processing system coupled with the imaging device, of the first reference image from features of the complementary second reference image;
    performing three-dimensional (3D) scene reconstruction for image data captured by the imaging device based on the identified features in the first reference image; and
    generating a 3D image from the 3D scene reconstruction for the image data,
    wherein the first reference image is a first grid of first dots and the complementary second reference image is a dropped dots grid formed by dropping a set of the first dots from the first grid.

2. The method of claim 1, wherein the set of dots are randomly dropped from the first grid of dots to form the dropped dots grid of the complementary second reference image, and wherein dots in the first reference image and the complementary second reference image correspond to features of the first reference image and the complementary second reference image.

3. The method of claim 2, wherein identifying features of the first reference image from features of the complementary second reference image comprises:
    for each first dot in the first grid of first dots of the first reference image, constructing a corresponding feature vector from nearest neighbor dots from the dropped dots grid of the complementary second reference image;
    for each first dot from the first grid of first dots of the first reference image in the first image data, generating the corresponding feature vector from the dropped dots grid of the complementary second reference image in the second image data; and
    generating an identification for each first dot from generated feature vectors, the identification of each first dot based on a match between the generated feature vector with a corresponding constructed feature vector.

4. The method of claim 1, further comprising:
    calibrating depth and coordinate dictionaries that translate pixel coordinate values of portions of image data of the scene to real world 3D coordinate values for corresponding portions of the image data; and
    performing the 3D scene reconstruction with the depth and coordinate dictionaries to provide real world 3D coordinate values for the identified features in the first reference image.

5. The method of claim 4, further comprising:
    for a plurality of depth planes,
        projecting the first reference image and the complementary second reference image on a moveable stage at a depth plane, and
        determining feature vector correspondence for features in the first reference image from features of the complementary second reference image;
    tracking image sensor pickup data for the features in the first reference image over the plurality of depth planes; and
    performing a regression analysis on the tracked image sensor pickup data using the tracked image sensor pickup data at each depth plane to generate a depth dictionary that translates image sensor pickup data for a portion of a captured image to a real world depth value for the portion of the captured image.

6. The method of claim 5, further comprising:
    for the plurality of depth planes, capturing image data, at a depth plane, of a printed image attached to the moveable stage, wherein the printed image comprises distinguishable features printed on the printed image having known distances there between, and wherein the distinguishable features correspond with the features of the first reference image; and
    for each feature in the printed image, performing a regression analysis on tracked image sensor pickup data for the distinguishable features of the printed image across the plurality of depth planes, the regression analysis performed based on a known depth of the moveable stage and the known distances between each feature in the printed image to generate a coordinate dictionary that translates image sensor pickup data for the portion of the captured image to real world coordinate values for the portion of the captured image.

7. The method of claim 6, wherein the image sensor pickup data comprises image sensor pixel coordinates that correspond with a centroid of pixels of the image sensor that picks up a feature in a captured image.

8. The method of claim 1, wherein the imaging device comprises an endoscope, and wherein the processing system comprises an image processing system communicably coupled with the endoscope.

9. The method of claim 1, wherein the projector is a digital micromirror device (DMD) projection device comprising a controllable matrix of micromirrors that direct light onto, or away from, the scene, further comprising:
controlling the DMD projection device to project the first reference image utilizing all of the micromirrors of the matrix; and
controlling the DMD projection device to project the complementary second reference image utilizing a randomly selected portion of the micromirrors of the matrix.

10. The method of claim 9, wherein the camera comprises a single lens and a single image sensor.

11. The method of claim 1, wherein generating the 3D image comprises storing the 3D image in a patient file, storing the 3D image in a pre-operative image registry, outputting the 3D image to a display device communicably coupled with the processing system, or a combination thereof.

12. The method of claim 1, wherein the grid of dots is a full grid of dots.

13. A non-transitory machine readable storage medium having instructions stored thereon, which when executed by a processing system, cause the processing system to perform a method comprising:
projecting, with a projector of an imaging device, a first reference image and a complementary second reference image on a scene;
capturing, with a camera of the imaging device, first image data and second image data including the first reference image and the complementary second reference image on the scene;
identifying features, with the processing system coupled with the imaging device, of the first reference image from features of the complementary second reference image;
performing three dimensional (3D) scene reconstruction for image data captured by the imaging device based on the identified features in the first reference image; and
generating a 3D image from the 3D scene reconstruction for the image data, wherein the first reference image is a first grid of first dots and the complementary second reference image is a dropped dots grid formed by dropping a set of the first dots from the first grid.

14. The non-transitory machine readable storage medium of claim 13, wherein the set of first dots are randomly dropped from the first grid of first dots to form the dropped dots grid of the complementary second reference image, and wherein dots in the first reference image and the complementary second reference image correspond to features of the first reference image and the complementary second reference image.

15. The non-transitory machine readable storage medium of claim 14, wherein identifying features of the first reference image from features of the complementary second reference image comprises:
for each first dot in the first grid of dots of the first reference image, constructing a corresponding feature vector from nearest neighbor dots from the dropped dots grid of the complementary second reference image;
for each first dot from the first grid of dots of the first reference image in the first image data, generating the corresponding feature vector from the dropped dots grid of the complementary second reference image in the second image data; and
generating an identification for each first dot from generated feature vectors, the identification of each first dot based on a match between the generated feature vector with a corresponding constructed feature vector.

16. The non-transitory machine readable storage medium of claim 13, further comprising:
calibrating depth and coordinate dictionaries that translate pixel coordinate values of portions of image data of the scene to real world 3D coordinate values for the corresponding portions of the image data; and
performing the 3D scene reconstruction with the depth and coordinate dictionaries to provide real world 3D coordinate values for the identified features in the first reference image.

17. The non-transitory machine readable storage medium of claim 13, wherein the imaging device comprises an endoscope, and wherein the processing system comprises an image processing system communicably coupled with the endoscope.

18. A system comprising:
an imaging device comprising
a projector to project a first reference image and a complementary second reference image on a scene, wherein the first reference image projected by the projector is a first grid of first dots and the complementary second reference image projected by the projector is a dropped dots grid formed by dropping a set of the first dots from the first grid, and
a camera to capture first image data and second image data including the first reference image and the complementary second reference image on the scene; and
a processing system communicably coupled with the imaging device to:
identify features of the first reference image from features of the complementary second reference image,
perform three dimensional (3D) scene reconstruction for image data captured by the imaging device based on the identified features in the first reference image, and
generate a 3D image from the 3D scene reconstruction for the image data.

19. The system of claim 18, wherein the set of dots are randomly dropped from the first grid of first dots to form the dropped dots grid of the complementary second reference image, and wherein dots in the first reference image and the complementary second reference image correspond to features of the first reference image and the complementary second reference image.

20. The system of claim 19, wherein the processing system identifies features of the first reference image from features of the complementary second reference image comprises the processing system to:
for each first dot in the first grid of dots of the first reference image, construct a corresponding feature vector from nearest neighbor dots from the dropped dots grid of the complementary second reference image, for each first dot from the first grid of dots of the first reference image in the first image data, generate the corresponding feature vector from the dropped dots grid of the complementary second reference image in the second image data, and generate an identification for each first dot from generated feature vectors, the identification of each first dot based on a match between the generated feature vector with a corresponding constructed feature vector.

21. The system of claim 18, further comprising the processing system to:

calibrate depth and coordinate dictionaries that translate pixel coordinate values of portions of image data of the scene to real world 3D coordinate values for the corresponding portions of the image data, and perform the 3D scene reconstruction with the depth and coordinate dictionaries to provide real world 3D coordinate values for the identified features in the first reference image.

22. The system of claim 18, wherein the imaging device comprises an endoscope, and wherein the processing system comprises an image processing system communicably coupled with the endoscope.

* * * * *